(12) United States Patent
Makizumi et al.

(10) Patent No.: US 6,825,036 B2
(45) Date of Patent: Nov. 30, 2004

(54) CELL USABLE IN SERUM-FREE CULTURE AND SUSPENSION CULTURE AND PROCESS FOR PRODUCING VIRUS FOR VACCINE BY USING THE CELL

(75) Inventors: Keiichi Makizumi, Kumamoto (JP); Kanako Masuda, Kumamoto-ken (JP); Yoichiro Kino, Kumamoto (JP); Sachio Tokiyoshi, Kumamoto (JP)

(73) Assignee: Juridical Foundation the Chemo-Sero-Therapeutic Research Institute, Kumamoto-ken (JP)

( * ) Notice: Subject to any disclaimer, the term of this patent is extended or adjusted under 35 U.S.C. 154(b) by 57 days.

(21) Appl. No.: 10/220,434

(22) PCT Filed: Mar. 2, 2001

(86) PCT No.: PCT/JP01/01599

§ 371 (c)(1),
(2), (4) Date: Sep. 3, 2002

(87) PCT Pub. No.: WO01/64846

PCT Pub. Date: Sep. 7, 2001

(65) Prior Publication Data

US 2003/0044962 A1 Mar. 6, 2003

(30) Foreign Application Priority Data

Mar. 3, 2000 (JP) .................................. 2000-059262

(51) Int. Cl.⁷ .................................................. C12N 5/00
(52) U.S. Cl. ........................ 435/325; 435/350; 435/383
(58) Field of Search ................................. 435/325, 350, 435/383

(56) References Cited

U.S. PATENT DOCUMENTS

| 5,348,877 A | 9/1994 | McKenna et al. |
| 5,906,939 A | 5/1999 | Salzmann |

FOREIGN PATENT DOCUMENTS

| WO | WO 96/15231 A2 | 5/1996 |
| WO | 97/37000 A1 | 10/1997 |
| WO | WO97/37000 A1 * | 10/1999 |

OTHER PUBLICATIONS

Merten et al.; Developments in Biological Standardization, vol. 98, 1999, pp. 23–37.
Merten et al.; Cytotechnology; vol. 30, No. 1–3, 1999, pp. 191–201.
Kessler et al.; Developments in Biological Standardization, vol. 98, 1999, pp. 13–21 and 73–74.
Perrin et al.; Vaccine, vol. 13, No. 13, 1995, pp. 1244–1250.
Yamane, Isamu "Baiyo Dobutsu Kabusaibo no Junka", vol. 29, No. 7, pp. 444–445, (1991).
Gaush et al.; Proc. Soc. Exp. Biol. Med., vol. 122, pp. 931–935 (1996).

* cited by examiner

Primary Examiner—James Housel
Assistant Examiner—Stacy B. Chen
(74) Attorney, Agent, or Firm—Birch, Stewart, Kolasch & Birch, LLP

(57) ABSTRACT

A novel MDCK-derived cell line (B-702) is provided that can be grown in the absence of fetal calf serum and in suspension culture for allowing a tank culture on the production scale and needs no carrier in suspension culture, as well as a process for producing virus for vaccine by using said cell line in a low-cost, highly safe and stable manner.

3 Claims, 1 Drawing Sheet

CELL USABLE IN SERUM-FREE CULTURE AND SUSPENSION CULTURE AND PROCESS FOR PRODUCING VIRUS FOR VACCINE BY USING THE CELL

This application is the national phase under 35 U.S.C. §371 of PCT International Application No. PCT/JP01/01599 which has an International filing date of Mar. 2, 2001, which designated the United States of America.

TECHNICAL FIELD OF THE INVENTION

The present invention relates to a cell line that can be grown in serum-free culture and in suspension culture without a carrier, and to production of a vaccine using said cell line. More particularly, the present invention relates to establishment of a cell line that can be grown without using serum and that can be grown in suspension culture without need of the cells to be adhered to any carrier, and a process for producing a vaccine with said cell line.

BACKGROUND OF THE INVENTION

In general, for production of a vaccine, there are widely used a growing chicken egg, a mouse brain, or primary cells or established cell lines from various animals such as chicken or ape. However, these conventional techniques involve various problems as mentioned below.

First, the use of a growing chicken egg necessitates management of chicken breeding, management of fertilized eggs to be adjusted to a vaccine production schedule, and laborious procedures including extensive purification for completely removing components derived from egg proteins while production. It is also problematic in view of animal protection.

Also in case of established cell lines, fetal calf serum as a cell growth factor must be added. However, its quality might vary among commercial products and it has a risk of contamination with mycoplasma, virus, or infectious proteins such as prion, and hence strict control of quality is required. Thus, a high-quality fetal calf serum such as one produced in New Zealand needs be used but is so costly that renders it unsuitable for production in industrial level.

Also among established cell lines where various kinds of viruses can be propagated, MDCK (Madin Darby Canine Kidney) cells are widely used in laboratory level (Proc. Soc. Exp. Biol. Med., 122, pp.931–935 (1966)). However, MDCK cells are much inclined to adhere to walls. Thus, the use of MDCK cells for an industrial large-scale culture is, due to its need for a large amount of culture medium, a culture vessel or a carrier for culture with a vast area, is disadvantageous in that: (1) it is extremely costly for equipment or a carrier; (2) it needs a step for removing cells adhered to a carrier and thereby some loss of cells is produced while recovery; and (3) cells are damaged due to contact between carriers (beads) according to culture conditions. Thus, it is not practical to use directly MDCK cells for vaccine production in view of cost and equipment.

Consequently, there has been a demand for establishing a process for producing a vaccine in a low-cost, highly safe and stable manner.

DISCLOSURE OF THE INVENTION

Under the circumstances, in order to obviate the disadvantages of the prior art as stated above, the present inventors have kept on investigating. As a result, the present inventors have established a novel cell line which can be grown without fetal calf serum and in suspension culture for enabling tank culture on the production scale and does not need any carrier in suspension culture. The present inventors also established a novel process for producing a vaccine without fetal calf serum to thereby enable providing a vaccine with low cost and high safety, and thus the present invention has been completed.

BEST MODE FOR CARRYING OUT THE INVENTION

Figure 1:
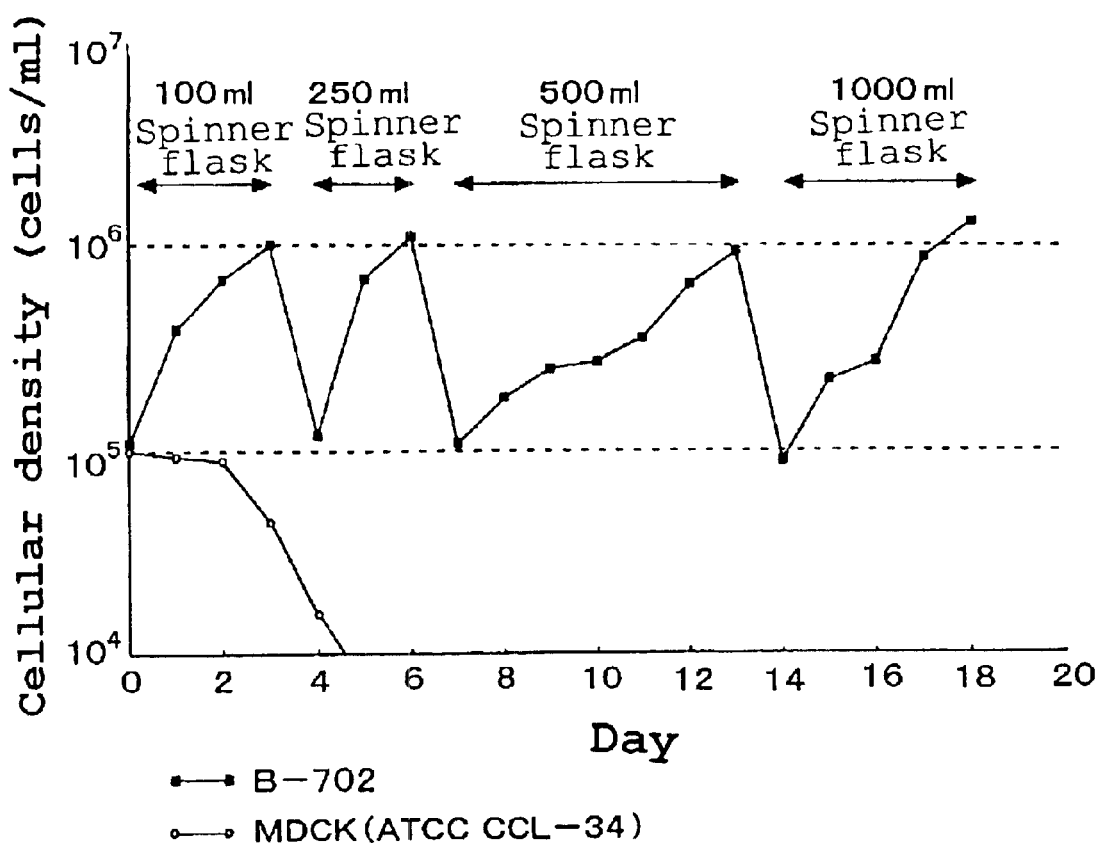
FIG. 1 shows growth of B-702 according to the present invention.

MDCK-derived cell line according to the present invention, which can be grown in serum-free culture and in suspension culture without a carrier, was prepared by the following steps:
(a) adapting MDCK cells to serum-free culture medium to prepare cells that can be grown in serum-free culture;
(b) applying the cells that can be grown in serum-free culture to suspension culture with a carrier to prepare cells that can be grown in suspension culture with a carrier; and
(c) applying the cells that can be grown in suspension culture with a carrier to suspension culture without a carrier to prepare cells that can be grown in suspension culture without need of a carrier.

More specifically, MDCK-derived cell line of the present invention was prepared in the following procedures.

MDCK cells were cultured in a monolayer in a 25 cm² culture flask containing Dulbecco Modified Eagle medium (hereinafter referred to as "D-MEM"; Gibco, Catalogue No. 11965-092) supplemented with 10% fetal calf serum (hereinafter referred to as "FCS") and non-essential amino acids (MEM Non-Essential Amino Acids Solution, Gibco, Catalogue No. 11140-050). After sufficient expansion of the cells, the cells were then cultured in the above medium containing 25% serum-free medium and subcultured upon confirming no abnormality in cells. A serum-free medium as used herein preferably contains no components from other animal species in view of safety. As an example, VP-SFM (Gibco, Catalogue No. 11681-020) was used herein. After subculture and sufficient expansion of the cells, the culture medium was replaced with D-MEM containing 50% VP-SEM. The procedures were repeated with a content of VP-SFM being increased to 75% and then 100% to adapt the cells to serum-free culture so that cells adapted to serum-free culture medium were ultimately established.

Then, the thus prepared cells adapted to serum-free culture medium were subjected to the following two approaches so that they can be grown in suspension culture without a carrier.

In the first approach, the cells adapted to serum-free culture medium were directly cultured in a spinner flask (Spinner Flask Complete, BELLCO, Catalogue No. 1965-00100) at 40 rpm with VP-SFM as a culture medium throughout the culture. When pH of the culture medium was lowered, a half of the medium alone was replaced with a fresh medium while leaving the cells to continue the culture. After about two-month culture, a population of cells was obtained that could be grown under this condition. However, a cellular density was at the most $5 \times 10^5$ cells/ml, but did not reach $1 \times 10^6$ cells/ml, the level necessary for industrialization.

In the second approach, the cells adapted to serum-free culture medium were adhered to a bead carrier Cytodex I (Pharmacia Biotec, Catalogue No. 17044801; bead concentration, 1 g (dry weight)/ml) and then cultured in a spinner flask (Spinner Flask Complete, BELLCO, Catalogue No. 1965-00100) at 40 rpm so that cells that can be grown under rotary shaking culture could firstly be produced. As a result, in about two months after initiation of culture, a population of cells was obtained that can be expanded and grown on the surface of the beads. Thereafter, a culture scale was enlarged to 250 ml, 500 ml and 1000 ml of a spinner flask (Spinner Flask Complete, BELLCO, Catalogue Nos. 1965-00250, 1965-00500, 1965-01000) while the cells were not treated with trypsin for release from the beads but a needed amount of VP-SFM medium and Cytodex I were added, to obtain a cell line that could be expanded to the culture scale. This cell line was then cultured in a spinner flask (Spinner Flask Complete, BELLCO, Catalogue No. 1965-00100) in the absence of a carrier Cytodex I with VP-SFM medium. As a result, after about a month, a cell line that could be grown in the absence of a carrier was obtained. This novel established cell line was named "B-702". B-702 is characteristic in that most of the cells are present in a unicellular state in suspension culture. Applicant has deposited B-702 at National Institute of Bioscience and Human-Technology Agency of Industrial Science and Technology, 1–3, Higashi 1-chome, Tsukuba-shi, Ibaraki-ken, Japan under accession number FERM BP-7449 (transferred from FERM P-17682 (original deposit made on Dec. 22, 1999); date of transfer to International Deposit, Feb. 9, 2001).

B-702 was then estimated for its growth. In most cases of established cell lines, about 3-fold expansion in cell number is considered to be optimum for expansion culture. On the contrary, in case of B-702, it was found that an initial cellular density of $1\times10^5$ cells/ml could be expanded to $1\times10^6$ cells/ml within about a week, i.e. 10-fold expansion. In the end, after the 10-fold expansion was performed, this cell line could be expanded to $3\times10^6$ cells/ml in a 1000 ml spinner flask starting from a 100 ml spinner flask.

Then, B-702 was estimated for its capacity to produce viruses. Three different influenza vaccine strains that were used in the season from 1998 winter to 1999 spring (A/Beijing/262/95[H1N1], A/Wuhan/359/95[H3N2], B/Mie/1/93) were inoculated at 0.001, 0.00003 and 0.0002 of M.O.I., respectively, into B-702 which were grown at a cellular density of $1\times10^6$ cells/ml in a 100 ml spinner flask. VP-SFM medium supplemented with 1% trypsin (Gibco, Catalogue No. 25200-072) was used for culture. After culture at 34° C. for 3 days, $1\times10^8$ PFU of viruses were propagated in each culture supernatant, which propagation of viruses was equivalent to that of MDCK cells cultured in a growing chicken egg or 10% fetal calf serum. Thus, it was found that B-702 could produce viruses in the absence of fetal calf serum and a carrier for cells.

Besides, it was confirmed that B-702 had a capacity to produce viruses including DNA viruses such as human herpes virus type 1 and type 2, and RNA viruses such as measles virus, mumps virus and rubella virus, indicating that any viruses capable of adapting to MDCK cells could be produced by B-702.

Such viruses include any animal viruses, including families of Orthomyxoviridae, Paramyxoviridae, Togaviridae, Herpesviridae, Rhabdoviridae, Retroviridae, Reoviridae, Flaviviridae, Adenoviridae, Picornaviridae, Arenaviridae and Poxviridae. Preferable viruses includes influenza virus, measles virus, mumps virus, rubella virus, HSV-1, HSV-2, rabies virus, RS virus, reovirus type 3, yellow fever virus, Japanese encephalitis virus, adenovirus types 1 to 47, poliovirus, Lassa virus and vacciniavirus. Most preferable viruses include influenza virus, human herpes virus type 1 and type 2, measles virus, mumps virus and rubella virus.

Thus, it was found that B-702 had wide utility as a cell line for virus production.

Viruses or viral antigens produced by MDCK-derived cell line, typically B-702, can be used as a source for preparing a vaccine.

B-702 according the present invention can be grown without need of fetal calf serum and a carrier for cells and hence allows for production of various useful substances, including vaccine, with a cheap medium in a stable and safe manner. Especially in association with production of influenza virus, when global pandemicity of new type virus occurred, which is worldwide concern in recent years, currently no technique or equipment is provided in Japan for urgently producing a needed amount of vaccine in a large scale. Accordingly, production of vaccine using B-702 is a much prosperous means for this purpose.

The present invention is illustrated in more detail by means of the following Examples to bring about a better understanding of the present invention, but should not be construed to be limited thereto.

EXAMPLE 1

B-702 was estimated for its growth with MDCK cells (ATCC CCL-34) as a control under the following conditions of culture medium, culture temperature, etc:

Culture medium: VP-SFM (Gibco, Catalogue No. 11681-020)
Additives: L-Glutamine (Gibco, Catalogue No. 25030-081), 2% (v/v)
  Gentamicin solution (Sigma, Catalogue No. G-1397), 0.1% (v/v)
Culture condition: 37° C., 5% $CO_2$, moist
Rotation of spinner: 40 rpm
Cellular density at the beginning of culture: about $1\times10^5$ cells/ml
Subculture Condition for Expansion:

At the time when a cellular density reached about $1\times10^6$ cells/ml, a culture was scaled up from 100 ml to 250 ml, 500 ml, and 1000 ml. At each stage where a culture is to be scaled up, a starting cellular density was adjusted to $1\times10^5$ cells/ml.

The results are shown in FIG. 1 wherein when MDCK cells were cultured in the absence of fetal calf serum and a carrier for cells, no increase in cell number was observed, the number of living cells drastically decreased on Day 3 and all the cells died out on Day 6. On the contrary, B-702 showed good increase in cell number even after scale-up of culture with increasing volume of a spinner flask.

EXAMPLE 2

B-702 was used to propagate viruses. The viruses employed herein were three different influenza vaccine strains that were used in the season from 1998 winter to 1999 spring with M.O.I. as indicated in Table 1.

TABLE 1

| Strain | M.O.I. |
|---|---|
| A/Beijing/262/95[H1N1] | 0.001 |
| A/Wuhan/359/95[H3N2] | 0.00003 |
| B/Mie/1/93 | 0.0002 |

Culture conditions were as follows:

Cellular density: $1\times10^6$ cells/ml
Culture scale: 100 ml spinner flask
Culture medium: as described in Example 1 but supplemented with 1% trypsin (Gibco, Catalogue No. 25200-072)
Rotation of spinner: 40 rpm
Culture temperature etc.: 34° C., 5% $CO_2$, moist
Duration of culture: 3 days It is commonly known that better viral propagation is observed at 34° C. than at 37° C. in culture of influenza virus and culture temperature currently used for vaccine production is also 34° C. Thus, viral culture in this test was performed at 34° C. It is also commonly known that, in culture of influenza virus with established cell lines, a protease that cleaves hemagglutinin (HA) is necessary for viral infection (U.S. Pat. No. 4,500,513). Thus, trypsin was included in a culture medium as a protease. A virus titer was measured in accordance with a plaque counting method as used for measuring a titer of influenza virus (Practice compendium in microbiology, 2nd ed., The University of Tokyo, The Institute of Medical Science, alumni association ed., Maruzen K. K., p. 205–206). Specifically, commonly used MDCK cells (ATCC-CCL-34) are cultured on a 6 well culture plate, into which 1×10$^6$ diluent of a supernatant of the above viral culture is inoculated. After inoculation, agarose is overlaid onto the monolayer of the cells and standing culture is performed in $CO_2$ incubator for 4 days. After completion of culture, formalin is added to fix the cells. The agarose layer is then removed, the cells are dyed with trypan blue and a plaque number formed by the virus is counted.

In three-day culture, all the cells died out. A culture supernatant was recovered and a viral titer was measured. As a result, as shown in Table 2, all the three vaccine viral strains exhibited a virus titer of not less than 1×10$^8$ PFU/ml, equivalent to that of allantoic fluid when viruses were propagated in growing chicken egg.

TABLE 2

| Virus | Virus titer (PFU/ml) |
| --- | --- |
| A/Beijing/262/95[H1N1] | 6.3 × 10$^8$ |
| A/Wuhan/359/95[H3N2] | 2.5 × 10$^8$ |
| B/Mie/1/93 | 1.2 × 10$^8$ |

EXAMPLE 3

MDCK cells intrinsically allow for propagation of various viruses. In order to investigate whether B-702 cell line inherited this sensitivity, B-702 was inoculated with human herpes virus type I (HSV-1) and type 2 (HSV-2) as DNA virus. Culture condition was as described in Example 2 except that trypsin was not included in the culture medium. Culture was continued for five days. Inoculation was performed as indicated in Table 3.

TABLE 3

| Inoculated Virus | Amount of inoculation |
| --- | --- |
| HSV-1 KOS strain | 0.01 ml |
| HSV-2 MS strain | 0.01 ml |

On Day 5, all the cells died out. Culture supernatant was recovered and a virus titer (PFU/ml) was measured by diluting by 1000-fold the culture supernatant to Vero cells derived from the kidney of African green monkey, and counting the formed plaques. The results proved that B-702 had a good capacity to propagate DNA viruses as shown in Table 4.

TABLE 4

| Inoculated Virus | Virus titer (PFU/ml) |
| --- | --- |
| HSV-1 | 1.2 × 10$^6$ |
| HSV-2 | 1.3 × 10$^6$ |

EXAMPLE 4

In order to investigate whether MDCK cells are capable of propagating other RNA viruses than influenza virus, inoculation was then performed for measles virus, mumps virus and rubella virus. Culture conditions were as described in Example 3 and culture was continued for five days. Inoculation was performed as indicated in Table 5.

TABLE 5

| Inoculated Virus | Amount of inoculation |
| --- | --- |
| Measles virus Ichinose strain (10$^5$ TCID$_{50}$/0.1 ml) | 0.01 ml |
| Mumps virus Enders strain (10$^4$ TCID$_{50}$/0.1 ml) | 0.01 ml |
| Rubella virus M33 strain (10$^7$ TCID$_{50}$/0.1 ml) | 0.01 ml |

On Day 5, all the cells died out. Culture supernatant was recovered and a virus titer was measured. For measurement of a virus titer, each of the above culture supernatant, diluted by 1,000-fold, 10,000-fold and 100,000-fold, was inoculated to each 6 wells of Vero cells cultured on a 24 well plate, which was then placed in a $CO_2$ incubator. After two-week standing culture, wells where cells were degenerated by viruses, i.e. CPE was demonstrated in the cells, were counted at each dilution, and 50% infection titer (TCID$_{50}$) was calculated by Kaerber's calculation method (Practice compendium in microbiology, 2nd ed., The University of Tokyo, The Institute of Medical Science, alumni association ed., Maruzen K. K., p. 205–206). The results proved that B-702 had a good capacity to propagate RNA viruses as shown in Table 6.

TABLE 6

| Inoculated virus | Virus titer (TCID$_{50}$) |
| --- | --- |
| Measles virus | 10$^{4.5}$ |
| Mumps virus | 10$^{6.8}$ |
| Rubella virus | 10$^{6.6}$ |

What is claimed is:

1. A process for preparing an MDCK cell line that can be grown in serum-free culture and in suspension culture without a solid carrier, which comprises the steps;

a) adapting MDCK cells to serum-free culture medium to prepare cells that can be grown in serum-free culture by a process of adjusting the medium from serum-containing medium to serum-free medium, b) applying the adapted MDCK cells to a suspension culture with a solid carrier to prepare cells that can be grown in suspension culture with a solid carrier; and c) applying the cells from step (b) that can be grown in suspension culture with a solid carrier to a suspension culture without a solid carrier to prepare cells that can be grown in suspension culture without need of a solid carrier.

2. The process of claim 1 wherein said serum-free culture medium used for serum-free culture does not contain components from animal species.

3. The process of claim 1 or 2 wherein said MDCK cell line is B-702.

* * * * *